United States Patent [19]

Cantafio, Jr.

[11] Patent Number: 5,062,860
[45] Date of Patent: Nov. 5, 1991

[54] PROSTHETIC ATTACHMENT

[76] Inventor: Frank A. Cantafio, Jr., 500 Center Rd., W. Seneca, N.Y. 14224

[21] Appl. No.: 475,854

[22] Filed: Feb. 6, 1990

[51] Int. Cl.[5] ............................................. A61F 2/58
[52] U.S. Cl. ........................................ 623/63; 623/65
[58] Field of Search ............................. 623/63, 64, 65

[56] References Cited

U.S. PATENT DOCUMENTS 1,874,183  8/1932  Geise ..................................... 623/63

Primary Examiner—Randall L. Green
Assistant Examiner—Randy Shay
Attorney, Agent, or Firm—Bean, Kauffman & Spencer

[57] ABSTRACT

An attachment for a prosthetic forearm useful to assist amputees in playing a stringed instrument is disclosed. The attached includes a chord finger that is adapted to extend across all of the strings of the instrument, and a note finger adapted to contact one or two strings of the instrument. The spacing between the fingers may be adjusted using the conventional prosthetic operating cable attached to a lever extending from the side of the chord finger.

11 Claims, 1 Drawing Sheet

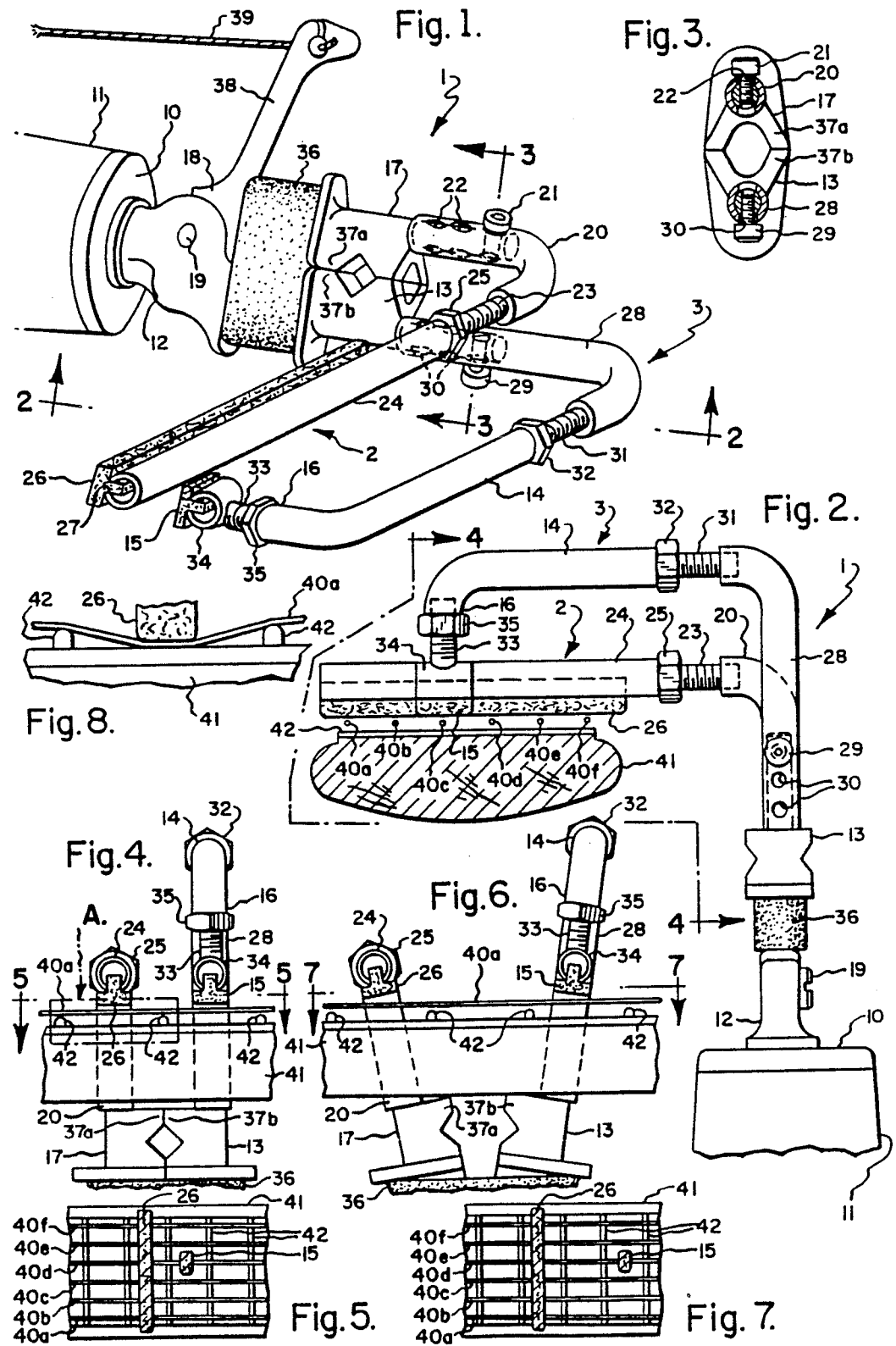

PROSTHETIC ATTACHMENT

BACKGROUND OF THE INVENTION

The present invention relates to prosthetic attachments, and more particularly to a prosthetic attachment adapted to assist upper limb amputees in playing a stringed instrument such as a guitar, or the like.

As used herein, the term "amputee" includes congenital and other deformities of an upper limb.

U.S. Pat. No. 3,992,975 issued Nov. 23, 1976 relates to a prosthetic attachment for disabled persons, such as amputees, in order to permit them to pick the strings of a guitar, or the like. This patent discloses a pick embedded in a hardened mass that is strapped to the forearm of the disabled individual.

Stringed instruments, such as guitars, banjos and mandolins, require depression of the springs against frets along the neck of the instrument in order to change the pitch of the strings, individually or as a group. Such instruments usually have the individual strings tuned to provide a musical chord when a pick, or the like, is moved across all of the strings.

Upper limb amputees are usually unable to properly depress the strings of a musical instrument to contact properly adjacent frets. Forearm and upper arm stumps usually have a substantially greater width than the separation between frets. Also, since upper limbs usually contain significantly more muscle and/or fatty tissue, and even if the strings can be depressed, proper notes or chords are not usually produced because of contact with one or more strings above the barred fret by the stump.

BRIEF DESCRIPTION OF THE PRESENT INVENTION AND DRAWINGS

The present invention is an attachment having two members for depressing the strings of an instrument, such as a guitar, one of the members, usually referred to as the chord finger, is adapted to extend across all the strings of the instrument and is utilized by the amputee by placing it between frets along the neck of the instrument and depressing the strings until they contact adjacent the frets. The other finger is adapted to contact one or two strings of the instrument. This note finger is used to selectively modify a chord produced using the chord finger by simultaneously depressing one or two of the strings at a fret higher than the location of the cord finger. The chord finger is movable to vary the spacing between the chord and note fingers and is usually moved by a cable, or the like. The attachment may be attached to an upper limb prosthesis through the conventional connection for the artificial hook and/or hand.

FIG. 1 is a perspective view of one embodiment of the attachment according to the present invention connected to an artificial arm;

FIG. 2 is a side view which illustrates the attachment relative to the neck of a stringed instrument shown in cross-section;

FIG. 3 is a sectional view along line 3—3 of FIG. 1;

FIG. 4 is a sectional top view along line 4—4 of FIG. 2 showing a portion of a stringed instrument;

FIG. 5 is a sectional top view along line 5—5 of FIG. 4;

FIG. 6 is a top view similar to FIG. 4, except the finger spacing has been increased;

FIG. 7 is a sectional top view along line 7—7 of FIG. 6; and

FIG. 8 is an enlargement of the portion A of FIG. 4 showing the relationship of a depressed string to adjacent frets.

DETAILED DESCRIPTION OF THE PRESENT INVENTION

Referring now to FIG. 1, attachment 1 is coupled to end 10 of prosthetic forearm 11 at one end of a first note finger portion 13. The second note finger portion 14 is coupled at one end to the first note finger portion 13 and carries a T-shaped string depressing pad 15. A movable chord finger 2 has a first leg 17 pivotally connected at one end 18 by pin 19. The other end of first leg 17 has an L-shaped connector 20 adjustably mounted thereto by screw 21 and a plurality of holes 22 in the connector. The other end of connector 20 has a threaded protrusion 23 with a second leg 24 threadably mounted thereto. Nut 25 is used to lock the second leg in adjustment on threaded protrusion 23. Elongated T-shaped pad 26 is carried by longitudinal slot 27 in second leg 24. Similarly, first note finger portion 13 has an L-shaped connector adjustably mounted thereto by screw 29 and holes 30. The second portion of the note finger 3 is adapted to thread over threaded protrusion 31 extending from connector 28 and is locked in position by nut 32. Threaded protrusion 33 carries slotted tip 34 and is threaded into distal end 16 for fine adjustments in the same direction provided by screw 29 and holes 30. Nut 35 is used to lock the adjustment after selection. One or more elastics 36 extending around first note finger portion 13 and first chord finger leg 17 urge the fingers toward each other until stops 37a and 37b are in contact. One end of lever 38 is connected to first leg 18 and the other end to cable 39, which is a conventional cable operated by the amputee.

Referring now to FIG. 2, it can be seen that elongated T-shaped pad 26 is adapted to extend across all of the strings 40a–40f of the fretted neck of musical instrument 41, while T-shaped string depressing pad 15 is adapted to depress only one or two strings. By threading second note finger portion 14 more or less onto threaded protrusion 31 of L-shaped connector 28, pad 15 is positioned over a selected string.

Referring now to FIGS. 4 and 5, it can be seen that in the normal position with elastic 36 biasing stops 37a and 37b into contact with each other, the spacing between elongated T-shaped pad 26 and T-shaped string depressing pad 15 is approximately the same as the distance between individual frets 42 spaced along instrument neck 41. With this arrangement, a chord, other than the open chord, is played by depressing pad 26 against all of the strings in between two adjacent frets 42 as shown in FIG. 8. Modification of the chord produced by pad 26 is achieved by simultaneously depressing one of the strings with pad 15. More than one modification of a selected chord may be achieved by changing the spacing between pad 15 and pad 26, as shown in FIGS. 6 and 7. This adjustment is achieved by pulling on cable 39 which causes the chord finger to pivot on pin 19 and stretching elastic 36. It will be appreciated that this variation in spacing may be achieved without otherwise adjusting the chord finger or note finger, and that the spacing illustrated in FIG. 4 can be reassumed when tension on cable 39 is relaxed.

The prosthetic attachment of the present invention enables an amputee to selectively play a chord, play a modified chord, or alternatively, play a note. Full advantage of the prosthetic attachment often requires adjustment of the tuning from that normally utilized for a given stringed instrument. For example, a guitar is normally played with the strings tuned to the notes E, A, D, G, B and E, in that order. By modifying the tuning of the fifth and sixth strings (B and E) to Bb and D, respectively, the type of chords available using the attachment of the present invention is increased. With the tuning of a guitar modified as noted above, minor chords are available by using only the chord finger of the prosthetic attachment. For example, the G minor chord of the open tuning may be changed to an A minor chord by barring the second fret, or a B minor chord by barring the fourth fret, ect. Major chords are produced, using the modified tuning, by adjusting tip 15 in a position to depress the fifth (Bb) string and depressing the fifth string with note finger pad 15 in addition to depressing all of the strings with chord finger pad 26. Thus, by barring the first fret with chord finger 2 and the fifth string at the second fret with note finger 3, a C major chord is produced. By a slight movement of the attachment relative to the guitar neck, an augmented chord may be produced by depressing both the fifth and sixth strings with note finger 3 at one fret above the fret barred by a chord finger 2. Similarly, diminished chords may be played by a slight movement of the attachment in the opposite direction in order to depress the fourth and fifth strings with note finger 3, as well as all of the strings at one fret lower with chord finger 2. A suspended chord is played by adjusting the spacing between the chord and note fingers to two frets with note finger 3 positioned over the fifth string (Bb). Those familiar with the use of artificial limbs and attachments will quickly recognize that by slight variations in the angle of the forearm relative to the longitudinal axis of the instrument neck, strings will be depressed either by the chord finger, the note finger, or both.

The following examples are offered to illustrate various combinations that may be achieved using modified tuning of a guitar and the attachment of the present invention.

EXAMPLE NO. 1

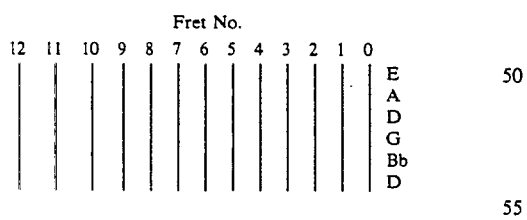

EXAMPLE NO. 2

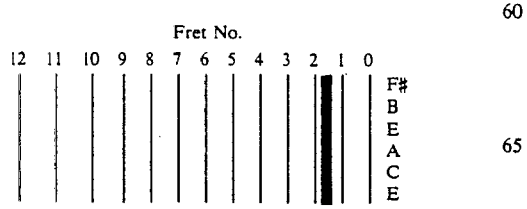

EXAMPLE NO. 3

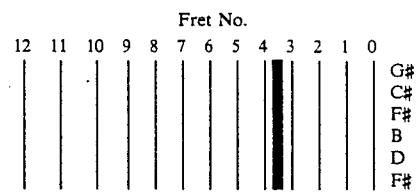

EXAMPLE NO. 4

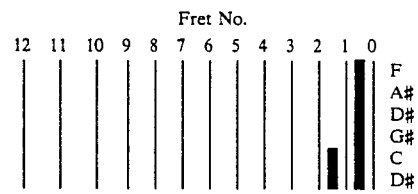

EXAMPLE NO. 5

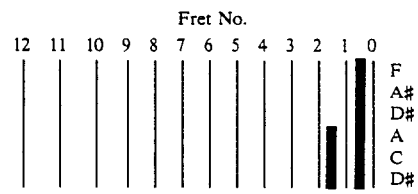

EXAMPLE NO. 6

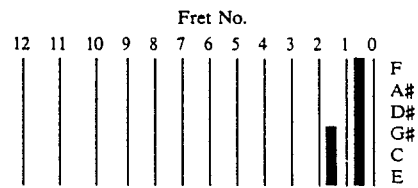

EXAMPLE NO. 7

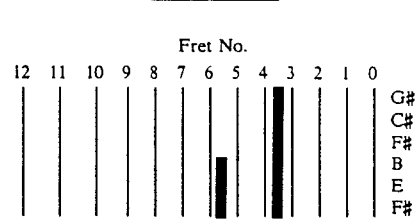

EXAMPLE NO. 8

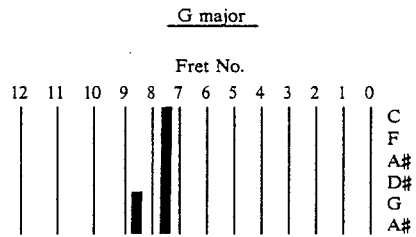

EXAMPLE NO. 9

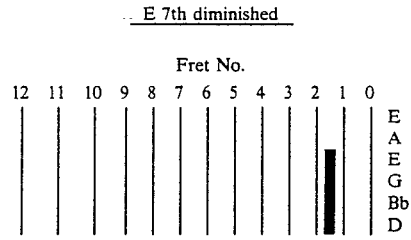

What is claimed is:

1. A prosthetic attachment for an upper limb to assist an amputee playing a stringed instrument which comprises, a chord finger, a portion of said chord finger extending in a direction generally normal to the remainder of said chord finger, a part of said portion being adapted to extend across an instrument neck having strings extending therealong, means to adjust the spacing between said part and the remainder of said finger, a note finger spaced from said chord finger, a portion of said note finger extending in a direction generally normal to the remainder of said note finger, and a piece of said note finger portion being adapted to engage a single string, means to adjust the spacing between said piece and the remainder of said note finger, and means to vary the spacing between said chord finger and said note finger, whereby a chord selected by engaging said chord finger with strings of an instrument can be selectively modified by engaging said note finger with a chosen one of the strings engaged by said chord finger.

2. A prosthetic attachment according to claim 1, further including pivot means connecting said chord finger to said note finger.

3. A prosthetic attachment according to claim 2, further including biasing means, said biasing means urging said chord finger toward said note finger.

4. A prosthetic attachment according to claim 3, wherein a lever extends from the remainder of said chord finger in a direction normal to a plane containing the remainder and said part and said spacing means includes a cable for connecting a portion of an amputee's body to the distal end of said lever.

5. A method of playing a stringed instrument having a plurality of strings extending along a fretted neck by using a prosthetic device having a chord finger, a note finger and means to vary the spacing between said fingers, which comprises the steps of tuning the instrument strings to provide a chosen open chord, depressing the strings with the chord finger at a position between adjacent frets to provide a selected chord related to the open chord and selectively depressing one of the strings with the note finger to provide a selected modified chord.

6. The method according to claim 5, wherein a plane is defined by the chord and note fingers and the plane is positioned parallel to the strings to modify the selected chord or oblique to the strings to play an unmodified selected chord.

7. The combination of a stringed instrument having a plurality of generally parallel strings extending along a fretted neck and a prosthetic attachment comprising an elongated note member having first and second portions, one end of said first portion being adapted for attachment to a prosthetic forearm, one end of said second portion being attached to the other end of said first portion, a first resilient pad attached to the distal end of said second portion, said first resilient pad being adapted engage a single one of the instrument strings, a chord member including first and second legs, one end of said first leg being pivotally attached to said note member for movement perpendicular to a second resilient pad attached to and extending along said second leg, said second pad being adapted to extend across the instrument strings, adjustment means for positioning the distal end of said note member at a chosen location along a line parallel to said second leg, and means to selectively move said chord member to vary the spacing between said note and chord members, whereby a chord related to the open-stringed tuning of said instrument may be played by depressing the strings with the chord member, if a plane containing said first and second pads is not parallel to the instrument strings and the related chord is modified, if the plane containing said first and second pads is parallel to the instrument strings.

8. The combination according to claim 7, further including means to bias said chord member toward said note member and a stop, said stop cooperating with said chord and note members to provide a minimum spacing between said chord and note members.

9. The combination according to claim 8, wherein said minimum spacing is about equal to the fret spacing.

10. The combination according to claim 9, wherein said instrument is a guitar and the strings are tuned to E, A, D, G, Bb and D.

11. The combination according to claim 10, where in said distal end is adjusted to depress two strings.

* * * * *